US00PP34082P2

(12) United States Plant Patent
van Noort

(10) Patent No.: US PP34,082 P2
(45) Date of Patent: Mar. 29, 2022

(54) ***ECHINACEA* PLANT NAMED 'NOECSEVEN'**

(50) Latin Name: ***Echinacea angustifolia* x *Echinacea purpurea***
Varietal Denomination: Noecseven

(71) Applicant: MARCO van NOORT BREEDING B.V., Warmond (NL)

(72) Inventor: Marco van Noort, Warmond (NL)

(73) Assignee: MARCO van NOORT BREEDING, B.V., Warmond (NL)

( * ) Notice: Subject to any disclaimer, the term of this patent is extended or adjusted under 35 U.S.C. 154(b) by 0 days.

(21) Appl. No.: 17/224,667

(22) Filed: Apr. 7, 2021

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
CPC ..... A01H 6/1448; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Echinacea* plant named 'Noecseven', characterized by its compact and upright plant habit; moderately vigorous growth habit; freely branching habit; strong flowering stems; freely flowering habit; single-type inflorescences with purplish red-colored ray florets and dark red-colored receptacle spine apices; and good garden performance.

2 Drawing Sheets

Figure 1:
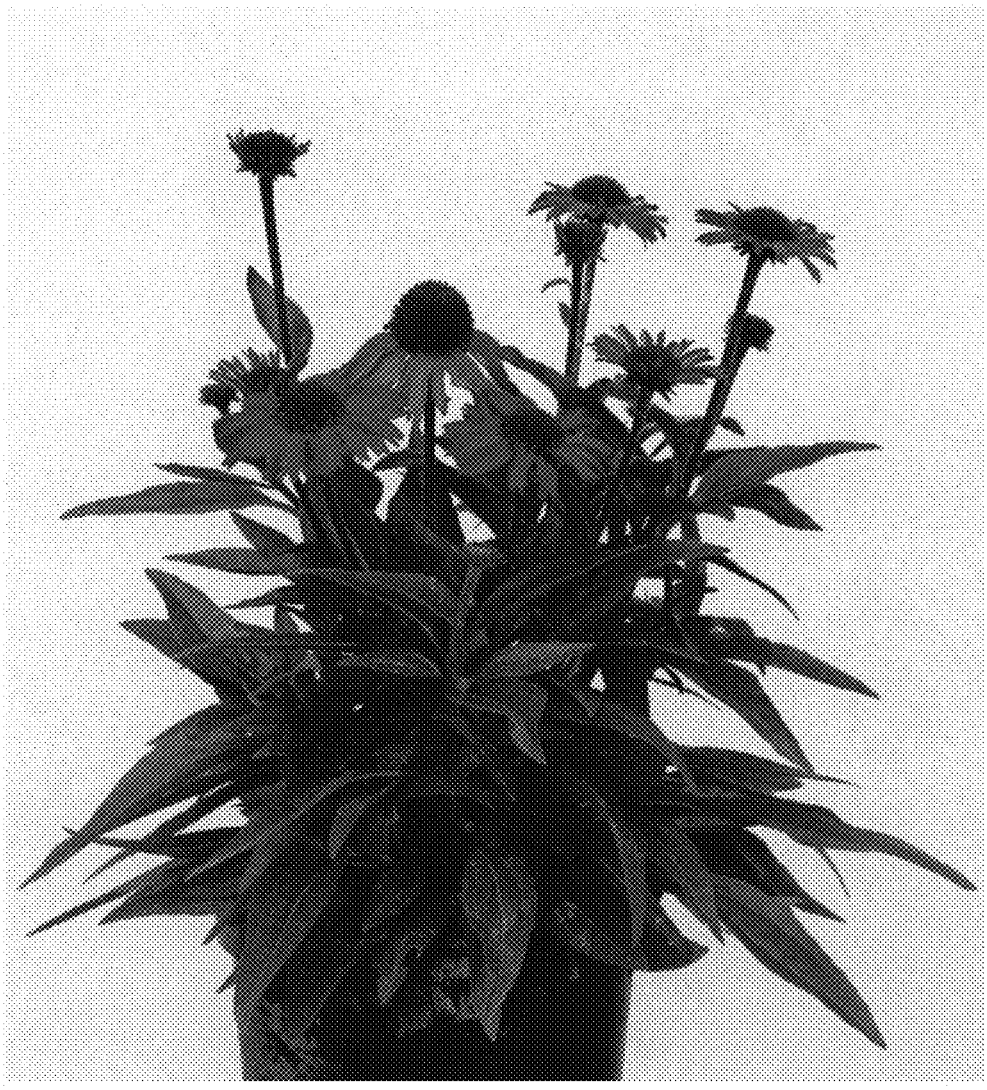

Botanical designation: *Echinacea angustifolia* x *Echinacea purpurea.*

Cultivar denomination: 'NOECSEVEN'.

STATEMENT REGARDING PRIOR DISCLOSURES BY THE INVENTOR & APPLICANT/ASSIGNEE

An European Community Plant Breeder's Rights application for the instant plant was filed by the Marco van Noort Breeding B.V. of Warmond, The Netherlands on Feb. 12, 2020, application number 2020/0426. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Echinacea* plant, botanically known as *Echinacea angustifolia* x *Echinacea purpurea*, and hereinafter referred to by the name 'Noecseven'.

The new *Echinacea* plant is a product of a planned breeding program conducted by the Inventor in Warmond, The Netherlands. The objective of the breeding program is to develop new compact *Echinacea* plants with unique and attractive ray floret coloration.

The new *Echinacea* plant is a naturally-occurring whole plant mutation of *Echinacea angustifolia* x *Echinacea purpurea* (also referred to as *Echinacea* hybrid) 'Sensation Pink', disclosed in U.S. Plant Pat. No. 26,593. The new *Echinacea* plant was discovered and selected by the Inventor as a single flowering plant from within a population of plants of 'Sensation Pink' in a controlled greenhouse environment in Warmond, The Netherlands in August, 2015.

Asexual reproduction of the new *Echinacea* plant by in vitro meristem culture in a controlled environment in Otrębusy, Poland since July, 2019 has shown that the unique features of this new *Echinacea* plant are stable and reproduced true to type in successive generations.

SUMMARY OF THE INVENTION

Plants of the new *Echinacea* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Noecseven'. These characteristics in combination distinguish 'Noecseven' as a new and distinct *Echinacea* plant:

1. Compact and upright plant habit.
2. Moderately vigorous growth habit.
3. Freely branching habit.
4. Strong flowering stems.
5. Freely flowering habit.
6. Single-type inflorescences with purplish red-colored ray florets and dark red-colored receptacle spine apices.
7. Good garden performance.

Plants of the new *Echinacea* can be compared to plants of the mutation parent, 'Sensation Pink'. Plants of the new *Echinacea* differ primarily from plants of 'Sensation Pink' in the following characteristics:

1. Plants of the new *Echinacea* are more compact than plants of 'Sensation Pink'.
2. Plants of the new *Echinacea* are more freely branching than plants of 'Sensation Pink'.
3. Plants of the new *Echinacea* are more freely flowering than plants of 'Sensation Pink'.
4. Plants of the new *Echinacea* have smaller inflorescences than plants of 'Sensation Pink'.

Plants of the new *Echinacea* can be compared to plants of *Echinacea purpurea* 'Summer Cloud', not patented. In side-by-side comparisons, plants of the new *Echinacea* differ primarily from plants of 'Summer Cloud' in the following characteristics:

1. Plants of the new *Echinacea* are more compact than plants of 'Summer Cloud'.
2. Plants of the new *Echinacea* are more freely branching than plants of 'Summer Cloud'.
3. Plants of the new *Echinacea* have smaller inflorescences than plants of 'Summer Cloud'.
4. Plants of the new *Echinacea* and 'Summer Cloud' differ in ray floret color as plants of the new *Echinacea* have lighter purplish red-colored ray florets than plants of 'Summer Cloud'.

BRIEF DESCRIPTION OF THE PHOTOGRAPHS

The accompanying photographs illustrate the overall appearance of the new *Echinacea* plant showing the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet (FIG. 1) is a side perspective view of a typical flowering plant of 'Noecseven' grown in a container.

Figure 2:
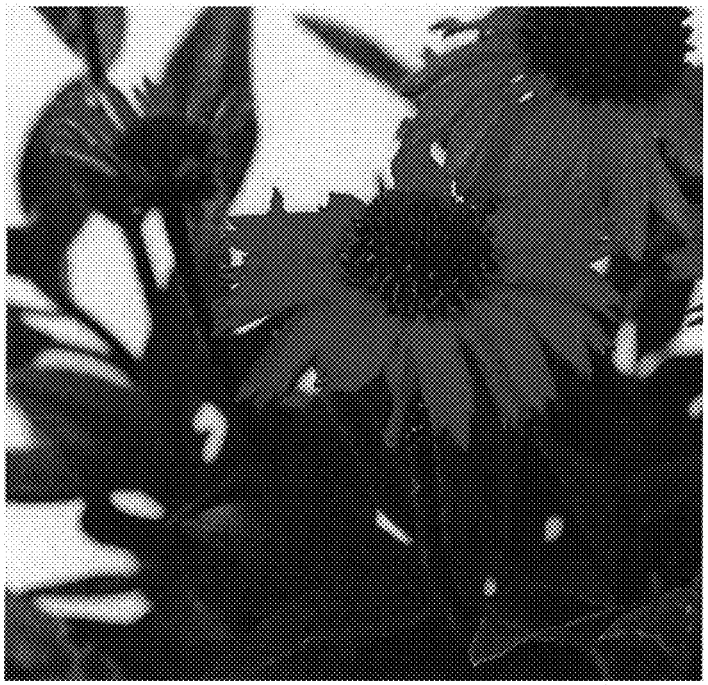

The photograph at the top of the second sheet (FIG. 2) is a close-up view of typical inflorescences of 'Noecseven' .

Figure 3:
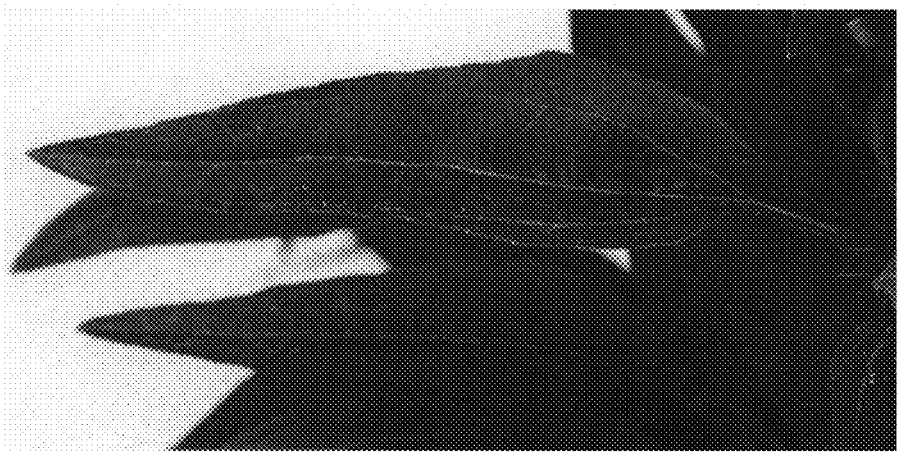

The photograph at the bottom of the second sheet (FIG. 3) is a close-up view of typical leaves of 'Noecseven'.

DETAILED BOTANICAL DESCRIPTION

The aforementioned photographs and following observations and measurements describe plants grown during the late summer in 15-cm containers in an outdoor nursery in Warmond, The Netherlands and under cultural practices typically used in commercial *Echinacea* production. During the production of the plants, day temperatures ranged from 16° C. to 25° C. and night temperatures ranged from 6° C. to 18° C. Plants were one year old when the photographs and description were taken. In the following description, color references are made to The Royal Horticultural Society Colour Chart, 2015 Edition, except where general terms of ordinary dictionary significance are used.

Botanical classification: *Echinacea angustifolia* x *Echinacea purpurea* 'Noecseven'.

Parentage: Naturally-occurring whole plant mutation of *Echinacea angustifolia* x *Echinacea purpurea* (also referred to as *Echinacea* hybrid) 'Sensation Pink', disclosed in U.S. Plant Pat. No. 26,593.

Propagation:

*Type*.—By in vitro meristem culture.

*Time to initiate roots, summer*.—About eight days at temperatures about 15° C. to 22° C.

*Time to initiate roots, winter*.—About 16 days at temperatures about 10° C. to 15° C.

*Time to produce a rooted young plant, summer*.—About 14 days at temperatures about 15° C. to 22° C.

*Time to produce a rooted young plant, winter*.—About 30 days at temperatures about 10° C. to 15° C.

*Root description*.—Fine, fibrous; typically white to brownish yellow in color, actual color of the roots is dependent on substrate composition, water quality, fertilizer type and formulation, substrate temperature and physiological age of roots.

*Rooting habit*.—Moderately freely branching; medium density.

Plant description:

*Plant form and growth habit*.—Herbaceous perennial; compact and upright plant habit; overall plant shape, broadly ovate to short oblong; freely basal branching habit with about eight primary lateral branches each with multiple secondary lateral branches developing per plant; moderately vigorous and slow growth rate.

*Plant height*.—About 28 cm.

*Plant diameter or spread*.—About 33.5 cm.

*Lateral branches*.—Length: About 15.4 cm. Diameter: About 4 mm. Internode length: About 3.1 cm. Aspect: About 15° from vertical. Strength: Strong. Texture: Moderately to densely pubescent; strigose, rough. Color: Close to 146B to 146C variably tinged with between N186C and 200B.

Leaf description:

*Basal leaves*.—Arrangement: Alternate, simple. Length: About 9.7 cm. Width: About 3 cm. Shape: Narrowly ovate, slightly carinate. Apex: Acute to narrowly acute. Base: Attenuate. Margin: Entire to very slightly angulate. Texture and luster, upper and lower surfaces: Moderately pubescent, strigose and rough; very slightly glossy. Venation pattern: Pinnate. Color: Developing leaves, upper surface: Close to 143A. Developing leaves, lower surface: Close to between 144A and 146B. Fully expanded leaves, upper surface: Close to NN137B; venation, close to 148B. Fully expanded leaves, lower surface: Close to 147B; venation, close to 145B.

*Cauline leaves*.—Arrangement: Alternate, simple. Length: About 7.9 cm. Width: About 2.4 cm. Shape: Narrowly ovate, slightly carinate. Apex: Acute to narrowly acute. Base: Attenuate. Margin: Entire to very slightly angulate. Texture and luster, upper and lower surfaces: Moderately pubescent, strigose and rough; very slightly glossy. Venation pattern: Pinnate. Color: Developing leaves, upper surface: Close to 143A. Developing leaves, lower surface: Close to between 144A and 146B. Fully expanded leaves, upper surface: Close to NN137B; venation, close to 148B. Fully expanded leaves, lower surface: Close to 147B; venation, close to 145B.

*Petioles, basal and cauline leaves*.—Length, basal leaves: About 6.6 cm. Diameter, basal leaves: About 2 mm by 2.5 mm. Length, cauline leaves: About 2.4 cm. Diameter, cauline leaves: About 2 mm by 2.5 mm. Texture, upper surface: Smooth, glabrous. Texture, lower surface: Sparsely pubescent. Color, basal leaves, upper surface: Close to 144C; towards the margins, close to 144A; at the base, close to 186A to 186B. Color, basal leaves, lower surface: Close to 144C; at the base, close to 186C to 186D. Color, cauline leaves, upper surface: Close to 144C; towards the margins, close to 144A. Color, cauline leaves, lower surface: Close to 144C.

Inflorescence description:

*Appearance*.—Single-type inflorescences with ray and disc florets arranged on a capitulum; inflorescences positioned upright above the foliar plane on upright and strong peduncles.

*Flowering habit*.—Freely flowering habit with about 16 developing and fully developed inflorescences per plant at one time.

*Fragrance*.—Faintly fragrant; sweet and pleasant.

*Time to flower*.—Plants flower continuously from early July to late September in The Netherlands; plants begin flowering about nine months after planting.

*Inflorescence longevity*.—Inflorescences maintain good substance for about three weeks on the plant; inflorescences persistent.

*Inflorescence buds*.—Height: About 1.6 cm. Diameter: About 3.8 cm. Shape: Flattened globular. Color: Close to 183A; immature ray florets, close to 67A and towards the base, close to 67B to 67C.

*Inflorescence size*.—Diameter: About 6.2 cm. Depth (height): About 2.5 cm. Disc diameter: About 2.6 cm.

*Receptacles*.—Height: About 6 mm. Diameter: About 5.5 mm. Shape: Ovoid. Color: Close to NN155B.

*Ray florets*.—Quantity and arrangement: About 19 to 24 arranged in a single whorl. Length: About 2.7 cm. Width: About 9 mm. Shape: Narrowly ovate to narrowly obovate; moderately carinate. Apex: Shallowly cleft to praemorse. Base: Cuneate. Margin: Entire. Texture and luster, upper surface: Smooth, glabrous; slightly velvety; matte. Texture and luster, lower surface: Smooth, glabrous; slightly glossy. Aspect: Horizontal to slightly downward, about 10° below horizontal; with development, reflexing downward, about 30° below horizontal. Color: When opening, upper surface: Close to 61B; towards the base, close to 61C. When opening, lower surface: Close to 61D; towards the margins, close to 60C. Fully opened, upper surface: Close to 60B and 61B; venation, similar to lamina; color becoming closer to 61B and 64B with development. Fully opened, lower surface: Close to 60C; towards the margins, close to 60B; venation, similar to lamina; color does not change with development.

*Disc florets*.—Quantity and arrangement: About 200 per inflorescence, arranged spirally at the center of the inflorescence. Length: About 9 mm. Diameter: About 2.5 mm. Shape: Tubular; proximally, 22.5% free, not fused. Apex: Acute. Base: Fused. Margin, free-part: Entire. Texture and luster, inner and outer surfaces: Smooth, glabrous; glossy. Color, when opening, inner and outer surfaces: Apex: Close to 144C; at the apex, close to 146C. Mid-section and base: Close to 145C to 145D. Color, fully opened, inner surface: Apex: Close to 185B. Mid-section: Close to 185D. Base: Close to 145B. Color, fully opened, outer surface: Apex: Close to 185C. Mid-section: Close to 185D. Base: Close to 145B.

*Receptacle spines*.—Quantity: One per disc floret; about 200 per inflorescence. Shape: Acicular. Apex: Acute. Base: Attenuate. Texture and luster: Smooth, glabrous; glossy. Color: Apex: Close to 185A; towards the mid-section, close to 42B. Mid-section: Close to 145B. Base: Close to 145D.

*Involucral bracts*.—Quantity per inflorescence: About 48 arranged in about three whorls. Length: About 5 mm. Width: About 2.5 mm. Shape: Ovate. Apex: Acute. Base: Cuneate. Margin: Entire. Texture, upper surface: Smooth, glabrous; at the margins, moderately to densely pubescent. Texture, lower surface: Moderately to densely pubescent. Color, upper surface: Close to NN137C. Color, lower surface: Close to 137B.

*Peduncles*.—Length, from uppermost cauline leaf to base of inflorescence: About 8.6 cm. Diameter: About 3 mm. Strength: Strong. Aspect: Upright to about 30° from vertical. Texture and luster: Moderately pubescent; strigose; moderately glossy. Color: Close to 144C, strongly mottled and striped with close to 183A to 183C.

*Reproductive organs*.—Androecium (present on ray and disc florets): Quantity per floret: Five. Filament length: About 2 mm. Filament color: Close to 157D. Anther length: About 3 mm. Anther shape: Lanceolate. Anther color: Close to 200A. Pollen amount: Scarce to moderate. Pollen color: Close to 17B. Gynoecium (present only on disc florets): Quantity per floret: One. Pistil length: About 6 mm. Stigma shape: Decurrent, unequal. Stigma color: Close to 185A. Style length: About 4 mm. Style color: Close to 145D. Ovary color: Close to 157C. Seeds and fruits: To date, seed and fruit development have not been observed on plants of the new *Echinacea*.

Pathogen & pest resistance: Plants of the new *Echinacea* have not been shown to be resistant to pathogens and pests common to *Echinacea* plants.

Garden performance: Plants of the new *Echinacea* have exhibited good garden performance and to tolerate rain and wind. Plants of the new *Echinacea* have been observed to tolerate high temperatures of about 35° C. and to be hardy to USDA Hardiness Zones 3 to 4.

It is claimed:

1. A new and distinct *Echinacea* plant named 'Noecseven' as illustrated and described.

* * * * *